United States Patent [19]
Szabo

[11] Patent Number: 5,681,315
[45] Date of Patent: Oct. 28, 1997

[54] BONE MARROW RASP

[76] Inventor: Zsolt Szabo, Reginoltstr. 17, 80933 Munchen, Germany

[21] Appl. No.: 654,912

[22] Filed: May 29, 1996

[30] Foreign Application Priority Data

May 31, 1995 [DE] Germany ............ 195 19 971.5

[51] Int. Cl.$^6$ .................................................. A61B 17/16
[52] U.S. Cl. ................................................. 606/85; 606/79
[58] Field of Search ............................ 606/85, 84, 79, 606/80

[56] References Cited

U.S. PATENT DOCUMENTS 5,019,082   5/1991   Frey et al. .
5,261,915   11/1993  Durlacher et al. ................ 606/85

FOREIGN PATENT DOCUMENTS 0296986   12/1988   European Pat. Off. .
0634145    1/1995   European Pat. Off. .
2547192   12/1984   France ................ A61B 17/16
9212906 U  1/1993   Germany .

Primary Examiner—Michael Buiz
Assistant Examiner—Daphna Shai
Attorney, Agent, or Firm—Anthony J. Casella; Gerald E. Hespos; Ludomir A. Budzyn

[57] ABSTRACT

A bone marrow rasp for forming bone cavities, particularly in femurs, having a tubular hollow body which is open at its distal end for the axially directed reception of bone material, has openings formed along its circumference which are in communication with the hollow space for the discharge of lateral bone material, and is connected along its outer surface with rasp elements which protrude beyond the outer surface and at least partially cover the openings.

3 Claims, 5 Drawing Sheets

BONE MARROW RASP

BACKGROUND OF THE SPECIFICATION

1. Field of the Invention

The present invention relates to a bone marrow rasp for forming hollow spaces in bones, particularly in femurs.

2. Description of the Prior Art

From Federal Republic of Germany 39 07 256 A1 there is already known a bone rasp for creating a shank bed for a hip joint endoprosthesis in the cavity of the human femur, which rasp has a lengthwise hollow body having an inner discharge channel. This discharge channel is connected by connecting holes with the outer surface of the body. Furthermore, cutting elements are provided distributed along the circumference of the body. The main body is closed at its distal end.

The human femur has a hard periosteum and an inner sponge-like mass known as the substantia spongiosa. This highly viscous sponge-like mass must be removed in order to create space for the prosthesis which is to be inserted. The prosthesis is inserted into the bone cavity which is formed and can also be fastened by means of bone cement.

For the preparation and formation of the desired bone bed, solid rasps were previously used which have the shape of the prostheses to be inserted and are hammered in increasing sizes one after the other axially into the bone. Such solid rasps are formed of solid material and press the liquid present in the substantia spongiosa outward. In this way, there is the danger, on the one hand, that the bone will burst due to the radial pressure. On the other hand, there is the danger that microparticles and particles of fat contained in the fluid will pass into the blood stream and, for instance, cause embolisms in the lung.

This risk of so-called fat embolism upon the implantation of cemented hip-joint prostheses or hip endoprosthesis has been known in orthopedics since 1970.

Since complications frequently occurred also in operations with cement-free prostheses, and in part even resulting in death, an intensive search started to determine the causes thereof. In accordance with the present state of knowledge, coaxial and radial pressure loads which result in pressure peaks within the bone are caused by the hammering-in of the traditional solid rasps. Bone marrow is introduced into the venous blood stream. The bone marrow components activate the blood coagulation system, as a result of which, in combination with the reduced rate of flow of the blood which is in any event present during an operation, microemboli are formed. These emboli or thrombi pass via the blood stream into the lungs and lead to a lung embolism, which is a potentially life-threatening syndrome. This syndrome is known by the name of fat embolism syndrome (FES).

The bone rasps known from the above-mentioned Federal Republic of Germany De 39 07 256 A1 constitute a first step toward the solution of the problem since bone material can be discharged through the laterally debouching holes. The action of this bone rasp is, however, insufficient since it has only slight differences from the full rasp and discharges only a part of the laterally encountered bone material.

In "Der Orthopäde", Vol. 24, Issue 2, Apr. 1995, reference is had in a large number of different articles by specialists in this field to the direct relationship between pulmonary fat embolisms and hip joint operations as a result of intramedullary pressure increase.

The object of the present invention is to provide a bone marrow rasp upon the use of which the pathological effect on the patient is reduced. In particular, it is the object of the invention to reduce the lateral pressure upon the introduction of the rasp into the bone and effectively to discharge the detached bone material.

By the reduction of the force of advance upon the rasping and drilling, the intramedullary pressure peaks can be reduced and the diffusing of bone marrow decreased. In this connection it is to be seen to it that the displacement of the bone marrow is reduced and thus a pressure build-up within the bone is avoided.

SUMMARY OF THE INVENTION

In accordance with the invention, there is proposed a bone marrow rasp for the forming of hollow spaces in bones, in particular the femur, which has a tubular hollow body which is open at its distal end for the axially directed reception of bone material, has openings formed along its circumference which are in communication with the hollow space for the leading away of lateral bone material, and has rasp elements along its outer surface.

The bone marrow rasp in accordance with the invention prevents excessive axial and radial pressure and permits a gentle preparation of the medullary space upon the implantation of endoprosthesis shanks. In the direction of advance, the rasp is open by a specially defined geometry with a thin wall thickness for a passage of material of up to 90 percent. In this way the lateral displacement of bone marrow volumes is considerably reduced. Bone liquid is conducted predominantly into the inside of the rasp so that the desired compacting effect of the substantia spongiosa can be retained. The weight of the rasp of the invention is slight due to the openings.

The bone marrow rasp of the invention constitutes a tube-like hollow body which is open at its distal end and which thus can be introduced without substantial radial displacement into the substantia spongiosa or the bone marrow. This is done with little application of force. The bone material which comes axially against the end of the hollow body is led away along the hollow space in the hollow body. Upon its introduction, the rasp builds up minimal pressure in the bone. On the other hand, the bone material which is detached laterally by the rasp elements is conducted directly into the openings adjacent to the rasp elements which are in communication with the hollow space and discharge the bone material effectively and rapidly. Since the hollow body is of slight wall thickness as compared with its diameter, the bone material conducted through the openings reaches the hollow space rapidly and can be effectively led away axially.

The wall thickness of the hollow body is preferably at most 2.5 mm, particularly at most 2 mm, and particularly preferably at most 1.5 mm. In this way, assurance is had that, upon the axial introduction of the bone marrow rasp into the bone, the lateral pressure is held at a minimum. The ratio of wall thickness to diameter of the hollow body is preferably at most 20%, particularly a maximum of 15%, and especially a maximum of 10%. These percentages have proven in tests to be preferred embodiments in order to assure static stability of the rasp.

The hollow body tapers down in cross section from its proximal end to its distal end and the rasp elements extend substantially paraxially in cross section. By this measure, assurance is had that the hollow body corresponds to the prosthesis to be introduced. The rasp elements protrude parallel to the center axis and thereby assure a gentle lifting off of lateral bone-wall material in the bone cavity which has already been formed. The material scraped off is discharged, upon axial advance of the bone marrow rasp, through the openings formed between rasp element and outer surface of the hollow body.

The rasp elements are preferably sharpened on their end edge in order effectively to peel off or scrape off the bone material.

The rasp elements preferably extend in radial groups along the circumference of the outer surface of the hollow body, the groups being offset axially from each other. In this way, the openings and corresponding rasp elements are distributed in mosaic fashion over the outer surface of the hollow body. In this way, a uniform homogeneous rasping action in circumferential direction is produced.

The bone marrow rasp is preferably formed by the bending of a perforated metal sheet and the connecting of its the axial edges. In this way, an economical and technically simple production of the bone marrow rasp is possible. The holes in the perforated metal sheet are preferably formed by stamping. In this way, the perforated sheet can be suitably prepared. The rasp elements are preferably formed by the bending-out or embossing of sections of the perforated sheet which adjoin the recesses. In this way, the rasp elements are prepared already in the perforated sheet. The openings result from the holes in the perforated sheet during the bending-out of the rasp elements. In this way, the entire arrangement and geometry of openings and rasp elements can be established already in the perforated sheet before it is bent.

It is preferred that the rasp elements have a radially surrounding contour. Each rasp element is thus formed by a radially surrounding cutting edge which is closed on itself, with which, in axial direction in front of it, a corresponding radially surrounding opening corresponds into which the bone material removed by the rasp element is introduced and discharged. In this embodiment, the effective rasp surface is clearly increased as compared with individual spatially limited rasp elements, and the lifting-off of bone marrow is effectively increased.

In another preferred embodiment, the rasp element are formed by a single helically extending cutting edge. In contradistinction to the previous embodiment, an individual helically surrounding cutting edge is thus formed which defines the rasp elements of the invention. This helical cutting edge corresponds to a correspondingly helical opening in axial direction in front of the cutting edge.

Furthermore, it is preferred that the surrounding rasp elements be connected together in axial direction by at least one connecting arm. The connecting arm effectively supports the surrounding rasp elements formed in the wall of the hollow body, so that they are not deformed upon introduction into the bone.

BRIEF DESCRIPTION OF THE DRAWINGS

Further advantages, features and possibilities of use of the present invention will become evident from the following description of two embodiments, read with reference to the drawing, in which.

DETAILED DESCRIPTION OF THE PREFERRED EMBODIMENT

Figure 1:
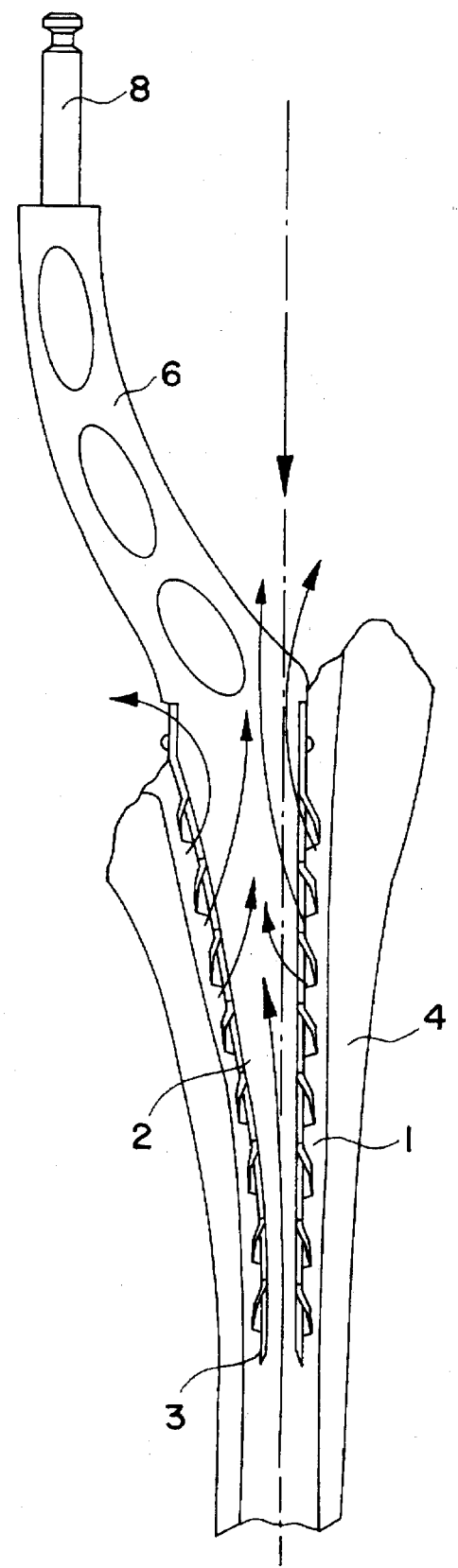
FIG. 1 is a cross section through an embodiment of a bone marrow rasp in accordance with the invention, introduced into a hip joint bone.

The bone marrow rasp shown in FIG. 1 has a thin-wall hollow body 2 which is connected with a substantially solid handle 6. The handle 6 on its part has a connection 8 for connecting the bone rasp to a pneumatic or electromechanical drive device. The hollow body 2 is introduced into a bone hollow 1 of a femur 4. The bone hollow 1 was formed by axial introduction of the hollow body 2 into the femur 4 of a patient. Thus, the outer contour of the bone hollow 1 corresponds to the outer contour of the hollow body 2. The hollow body 2 has a distal end 3, at which it is open. From this distal end 3 the hollow body widens out in axial direction. Furthermore, the hollow body 2 has openings (not shown) arranged laterally in its wall through which the laterally impinging bone material is discharged axially through the inner cavity. The arrows indicate the direction of the discharged bone material which passes, on the one hand, axially through the inlet opening formed at the distal end and through the lateral entrance openings into the inner hollow space the hollow body 2.

Figure 3:
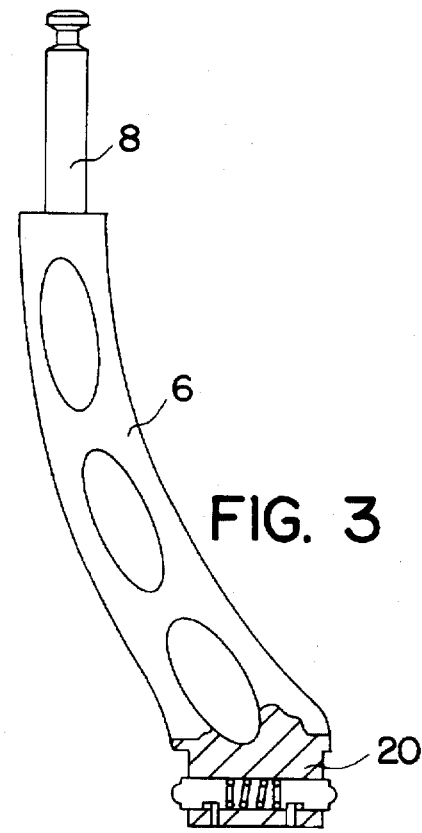
FIG. 3 shows a handle of a bone marrow rasp corresponding to the hollow body of FIG. 2.
Figure 2:
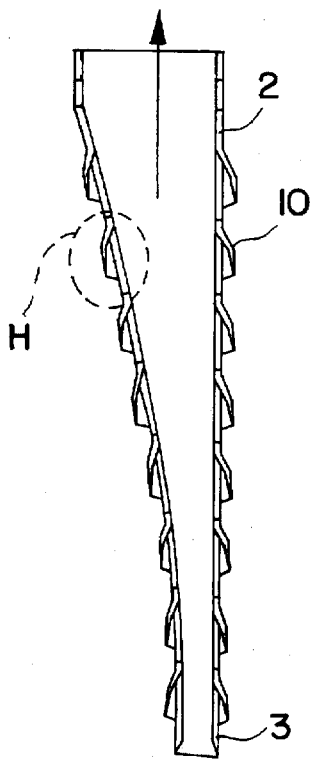
FIG. 2 shows another embodiment of a hollow body of a bone marrow rasp in accordance with the invention.

FIGS. 2 and 3 shows further parts of another embodiment of a bone marrow rasp in accordance with the invention. FIG. 2 shows the corresponding hollow body 2, which tapers down from its proximal end to its distal end 3 and has rasp elements 10 and corresponding openings (not shown) along its circumference. The corresponding handle 6 has a connecting part 20 for connection to the hollow body 2. In this way, the handle 6 can be used for hollow bodies of different dimension, for instance of increasing cross sections. The connection element 8 serves for connection to a pneumatic or electromechanical drive device.

Figure 4A:
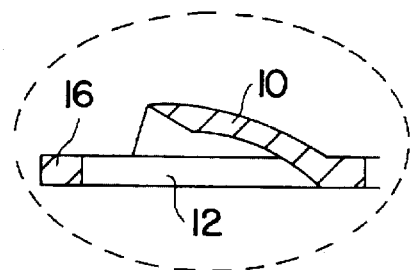
FIG. 4a shows a longitudinal section through the detail H in FIG. 2.
Figure 4B:
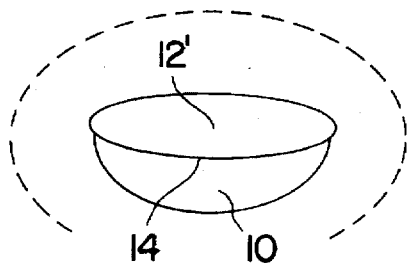
FIG. 4b is a top view of the detail H in FIG. 2.
Figure 4C:
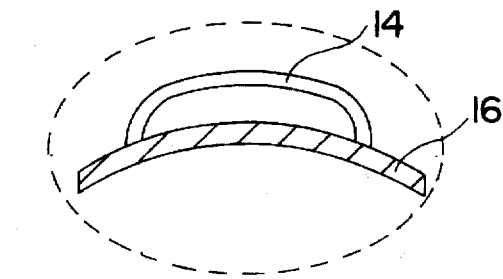
FIG. 4c is a bottom view in axial direction of the detail H of FIG. 2.

FIGS. 4a to 4c show details of the hollow body 2 from the portion of FIG. 2 indicated in the dashed-line circle H. FIG. 4a is a longitudinal section through the hollow body 2 in the region of a rasp element 10. The rasp element 10 extends protruding axially from the outer surface or wall surface of the hollow body 2 and has a sharpened end edge 14. Opposite the rasp element 10, an opening 12 is formed in the outer surface of the hollow body 2, the opening extending between the base point of the rasp element 10 and a facing section 18 of the outer surface. The rasp element 10 at least partially covers the opening 12. The rasp elements 10 extend substantially paraxially to the center axis of the hollow body 2.

FIG. 4b shows a side view of the detail H of FIG. 2, from which it can be seen that the rasp element 10 has the shape of a curved surface which forms a sharpened end edge 14 and is connected at all other edges to the sections of the outer surface which adjoin the opening 12, so that the surface 10 at least partially surrounds the opening 12 in envelope form. From the view in FIG. 4b, it can also be noted that the rasp element 10 radially covers only a part of the entire opening 12, while a hole 12' is not covered by the rasp element 10. This hole 12' is formed by stamping in the perforated sheet used for the production. The rasp element 10 is formed by the embossing of a perforated sheet provided with holes 12' in the region of the holes 12'. Thus the openings 12 are formed by the originally stamped regions of the holes 12' and the recesses in the outer surface of the hollow body 2 which result from the bending-up or embossing of the rasp elements 10.

FIG. 4c is a bottom view in axial direction of the detail H of FIG. 2, in which one can note the edge 16 in the outer surface as well as the sharpened end edge 14 of the rasp element 10.

Figure 4D:
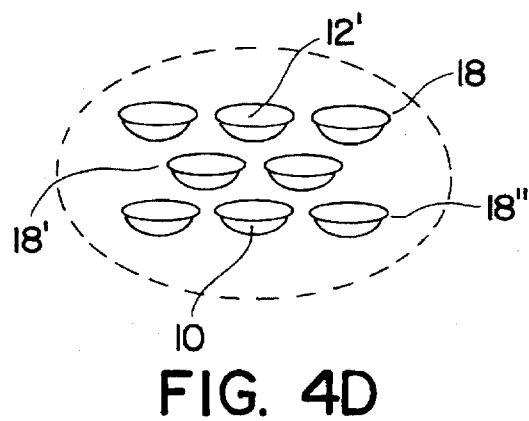
FIG. 4d is a side view of the hollow body of FIG. 2.

FIG. 4d shows several rasp elements 10 developed in the form of a group 18 in radial circumferential direction in the hollow body 2 and corresponding holes 12'. Adjoining the group 18 there is a group 18' with rasp elements which are staggered by half a spacing with respect to the rasp elements of the group 18. Adjoining the group 18', in its turn, there is a group 18" which has rasp elements which are staggered by half a spacing with respect to the group 18' and are substantially aligned with the rasp elements of the group 18.

The bone marrow rasp of the invention provides a satisfactory possibility for forming shank beds for prosthesis shanks in bones, the pathological effect being reduced upon its use. During the formation of the hollow space in the bone, the external pressure is minimized and the bone components of the substantia spongiosa and the bone marrow which are lifted off are effectively discharged axially along the cavity. Thus, the bone marrow rasp of the invention permits easy penetration into the bone, with clearly reduced hammering force. As compared with traditional solid rasps there is a considerable saving of material with a particularly rational manufacture from perforated sheets.

Figure 5:
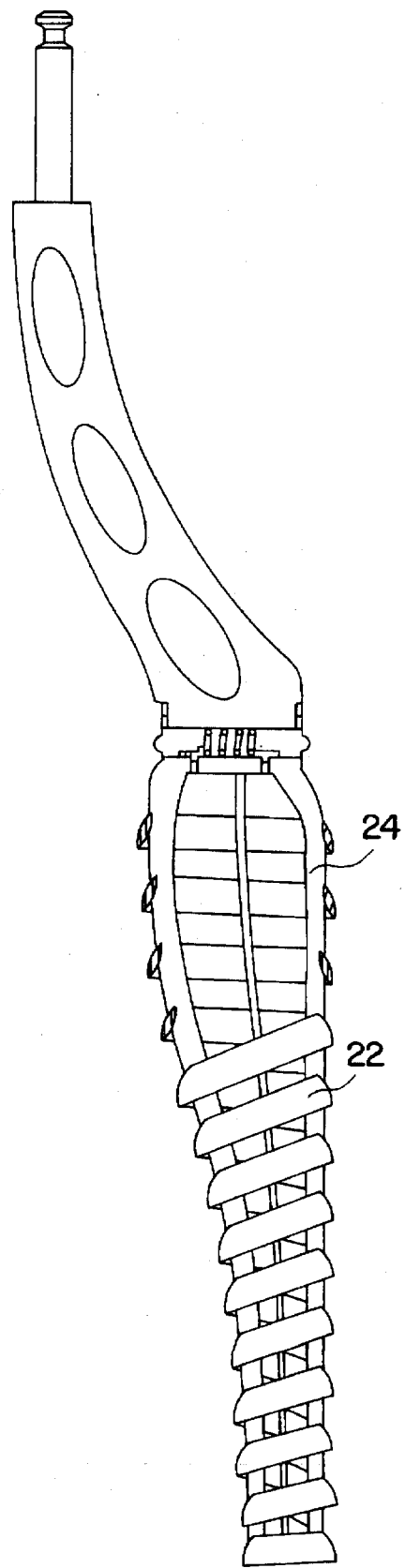
FIG. 5 is a side view of another embodiment of a bone marrow rasp according to the invention with a helical cutting edge.
Figure 6:
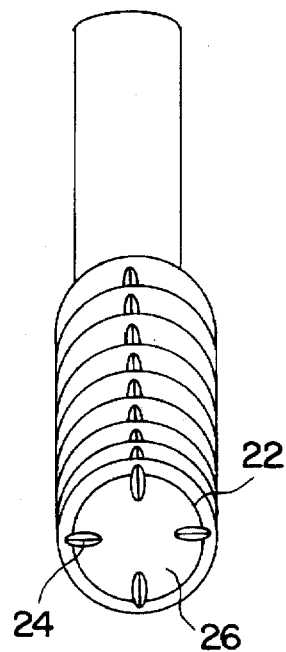
FIG. 6 shows the rasp of FIG. 5 in a perspective view from the front.

FIGS. 5 and 6 show another embodiment of a bone marrow rasp in which the rasp elements are formed by a helically wound cutting edge 22 which is guided around lateral arms 24. Four lateral arms 24 arranged 90 degrees apart are provided, they being closed off axially at the end by a closure ring 26.

Figure 7:
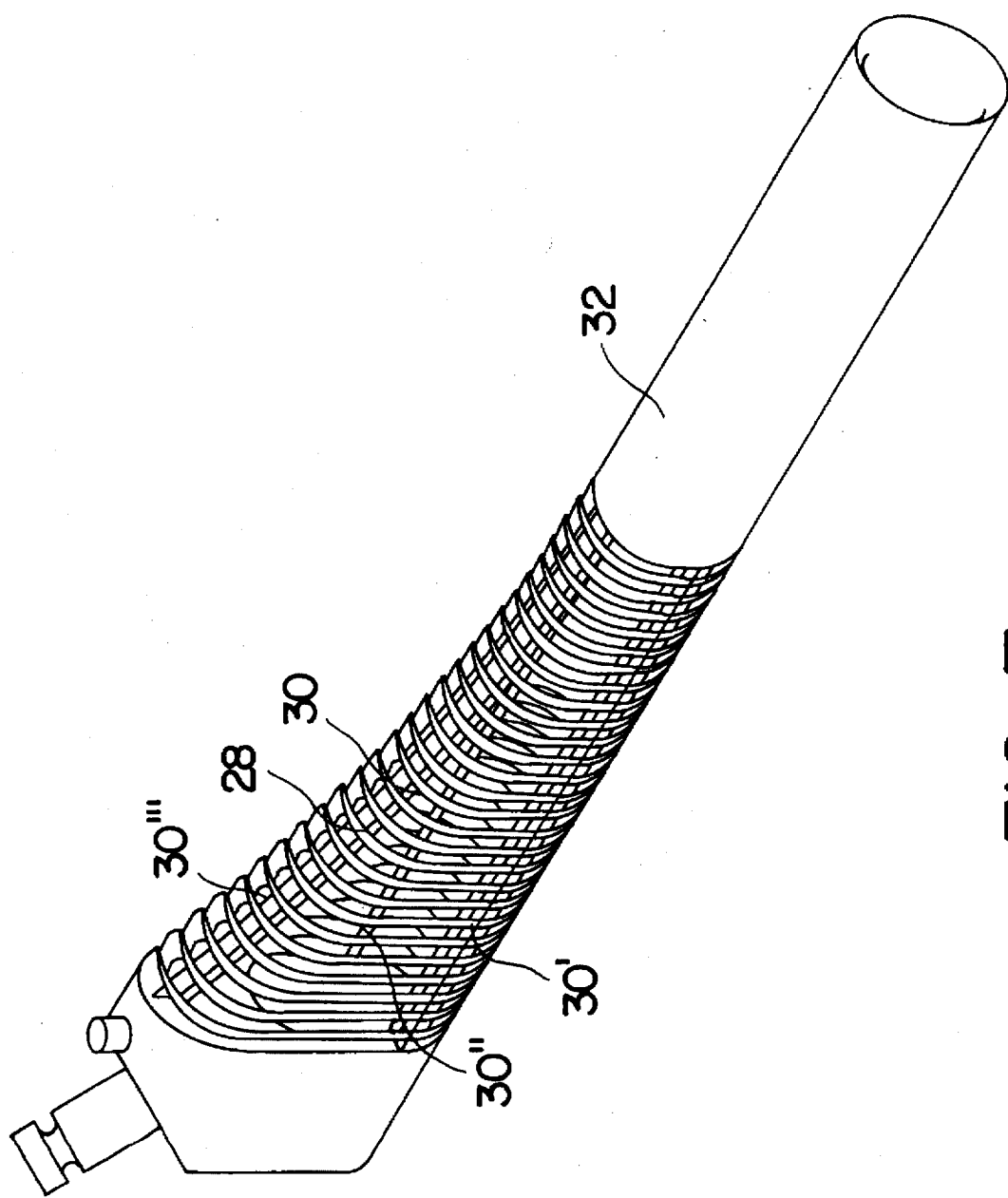
FIG. 7 shows another embodiment of a rasp in accordance with the invention, seen in perspective.
Figure 8:
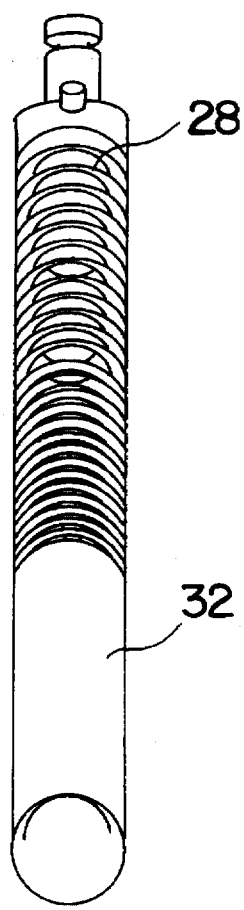
FIG. 8 shows the rasp of FIG. 7, seen from the front in perspective.
Figure 9:
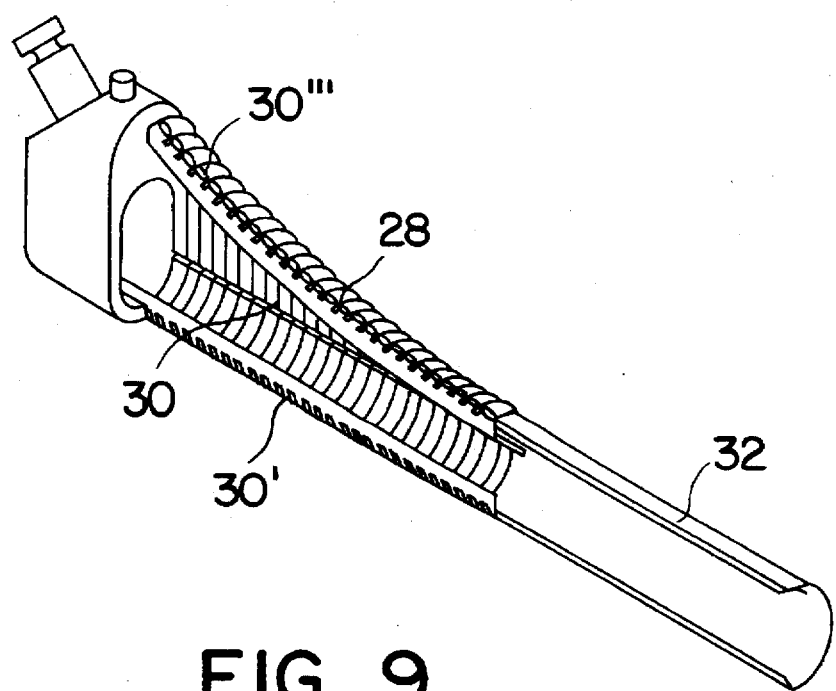
FIG. 9 shows the rasp of FIG. 7 in section.

FIGS. 7, 8 and 9 shows another embodiment of a bone marrow rasp with surrounding spirally shaped or helically shaped rasp elements which are formed by a single helical cutting edge 28. By the radially spirally extending cutting edge 28, blade-like rasp elements are formed the cutting edges of which extend substantially in axial direction and serve effectively for the lifting-off of bone material. The cutting edge 28 is formed in the wall of the hollow body or part of said wall so that an opening cooperating with the cutting edge 28 also extends helically. In FIG. 7, four connecting arms 30, 30', 30", 30'" are formed which pass through or connect the rasp elements in axial direction so as to increase their stability and stiffness. At the end, the hollow rasp is closed by a tube-shaped, non-tapered tubular element 32 which closes the hollow rasp off at the end and does not contain any rasp elements.

The embodiments of FIGS. 5 to 9 are preferably produced by high-pressure casting from a medically compatible material.

I claim:

1. A bone marrow rasp having opposed proximal and distal ends, said proximal end defining a handle, a plurality of circumferentially spaced connecting arms extending distally from the handle, a hollow tube secured to said connecting arms at locations distally of said handle and extending to said distal end of said rasp, a plurality of axially spaced circumferentially extending blades between said handle and said tube, each said blade having a proximal edge rigidly supported on the connecting arms and a distal cutting edge spaced outwardly from said connecting arms for lifting said bone marrow and guiding said bone marrow interiorly of said blades.

2. A bone marrow rasp according to claim 1, wherein said blades are parallel.

3. A bone marrow rasp according to claim 1, comprising four said connecting arms.

* * * * *